(12) United States Patent
Kunis et al.

(10) Patent No.: US 6,491,681 B1
(45) Date of Patent: Dec. 10, 2002

(54) HANDLE FOR USE WITH STEERABLE DEVICE FOR INTRODUCING DIAGNOSTIC AND THERAPEUTIC ELEMENTS INTO THE BODY

(75) Inventors: Christopher G. Kunis, San Jose, CA (US); Russell B. Thompson, Los Altos, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/544,520

(22) Filed: Apr. 6, 2000

(51) Int. Cl.[7] .............................................. A61M 25/09
(52) U.S. Cl. .................................. 604/528; 604/164.13
(58) Field of Search ................................ 604/523, 528, 604/533, 164.13, 164.01, 165.03, 95.01, 264

(56) References Cited

U.S. PATENT DOCUMENTS

| | | | |
|---|---|---|---|
| 4,586,923 A | 5/1986 | Gould et al. | 604/95.04 |
| 4,664,113 A | 5/1987 | Frisbie et al. | 606/194 |
| 4,757,827 A | 7/1988 | Buchbinder et al. | 600/585 |
| 4,960,411 A | 10/1990 | Buchbinder | 604/95.01 |
| 5,030,204 A | 7/1991 | Badger et al. | 604/95.04 |
| 5,114,403 A | 5/1992 | Clarke et al. | 604/95.04 |
| 5,391,146 A | 2/1995 | That et al. | 604/95.01 |
| 5,419,340 A | 5/1995 | Stevens | 600/585 |
| 5,419,764 A | 5/1995 | Roll | 604/95.04 |
| 5,472,017 A | 12/1995 | Kovalcheck | 138/103 |
| 5,935,102 A | 8/1999 | Bowden | 604/95.04 |
| 5,938,616 A | 8/1999 | Eaton | 600/463 |
| 6,059,739 A | 5/2000 | Baumann | 600/585 |
| 6,066,125 A | 5/2000 | Webster, Jr. | 604/528 |

FOREIGN PATENT DOCUMENTS

| | | |
|---|---|---|
| WO | WO 99/62585 | 12/1999 |
| WO | WO 00/22981 | 4/2000 |

*Primary Examiner*—Edward K. Look
*Assistant Examiner*—Dwayne White
(74) *Attorney, Agent, or Firm*—Henricks, Slavin & Holmes LLP (57) ABSTRACT

A handle apparatus includes a handle body, a trolley member that may be secured to a steering wire, and a steering member operably connected to the trolley member. Rotation of the trolley member is prevented and rotation of the steering member axially repositions the trolley member and steering wire.

38 Claims, 9 Drawing Sheets

HANDLE FOR USE WITH STEERABLE DEVICE FOR INTRODUCING DIAGNOSTIC AND THERAPEUTIC ELEMENTS INTO THE BODY

BACKGROUND OF THE INVENTIONS

1. Field of the Inventions

The present inventions relate generally to handle apparatus for use with a steerable device for introducing diagnostic and therapeutic elements into the body.

2. Description of the Related Art

There are many instances where physicians must introduce diagnostic and therapeutic apparatus, such as diagnostic and therapeutic electrodes, ultrasound transducers, biopsy devices and other surgical tools, into the body. The diagnostic and therapeutic apparatus are often carried by catheters, which allow physicians to gain access to the body in a minimally invasive manner by way of bodily lumens. In cardiac treatment, for example, a catheter is advanced through a main vein or artery into the region of the heart that is to be treated.

One method of introducing diagnostic and therapeutic apparatuses into the body is to introduce a tubular member (typically a "sheath") into the vicinity of the targeted region. A diagnostic or therapeutic apparatus is then passed through the tubular member to the targeted region. If necessary, the diagnostic or therapeutic apparatus may be removed after its function is performed, but the tubular member left in place, so that other apparatus may be advanced to the targeted region to complete the diagnostic and/or therapeutic procedure.

Precise placement of the diagnostic or therapeutic apparatus is very important, especially in those procedures concerning the heart. To that end, some conventional sheaths are guided to the targeted region with a steerable catheter that is located within the sheath lumen. Once the sheath reaches the targeted region, the steerable catheter is removed from the sheath and a catheter carrying the diagnostic or therapeutic apparatus is advanced through the lumen. This type of sheath lacks any onboard steering mechanism. As a result, redeployment of the distal portion of the sheath, even to a region in close proximity to the initially targeted region, requires the withdrawal of the diagnostic or therapeutic apparatus and the reintroduction of the steering catheter.

Other conventional sheaths include a steering mechanism that allows the physician to deflect the distal portion of the sheath. The steering mechanism consists primarily of one or more steering wires. One end of each steering wire is secured to the distal end of the sheath, while the other end is secured to a steering control device, such as the rotating cam and steering control knob arrangement commonly found in steerable catheters. Rotation of the control knob causes one of the wires to impart a pulling force on the distal portion of the sheath, thereby causing the distal portion of the sheath to deflect. To promote steerability, the distal portion of the sheath (which is relatively short) is typically formed from relatively soft, flexible material. Conversely, the proximal portion (which is relatively long) is formed from relatively hard, less flexible material that provides better torque transmission properties.

The inventors herein have determined that there are a number of shortcomings associated with handles conventionally used with steerable sheaths. For example, some conventional handles include a luer fitting on the proximal end thereof and a rotatable steering device that is operably connected to a steering wire. A tubular device is connected to the luer fitting on the handle with a Toughy-Borst or other connector. Rotation of the steering device causes the portion of the handle with the luer fitting to move axially relative to the remainder of the handle. This can be problematic because the tubular device typically remains in place, thereby causing the handle (and the sheath connected to the handle) to move back and forth and/or rotate.

The inventors herein have also determined that some conventional handles tend to roll around on the patient when the steering knob is rotated. As such, these handles must be operated with both hands or fixedly secured to the patient.

Some conventional handles include a strain relief element that must be glued or otherwise attached to the handle. The inventors herein have determined that the design of conventional strain relief elements adds extra steps to the manufacturing process and, accordingly, increases the cost of the handle.

SUMMARY OF THE INVENTIONS

Accordingly, the general objective of the present invention is to provide an apparatus that avoids, for practical purposes, the aforementioned problems. In particular, one objective of the present invention is to provide a handle apparatus for use with a steerable device that does not suffer from some or all of the aforementioned problem associated with conventional handles.

In order to accomplish some of these and other objectives, a handle apparatus in accordance with one embodiment of a present invention includes handle body defining an inner chamber, a trolley member slidably located at least partially within the inner chamber, adapted to be connected to a steering wire and defining a trolley member lumen, and a steering member rotatably coupled to handle body and operably connected to the trolley member such that rotation of the steering member axially repositions the trolley member, the steering member including a steering member lumen substantially axially aligned with the trolley member lumen.

In order to accomplish some of these and other objectives, a handle apparatus in accordance with one embodiment of a present invention includes a handle body defining an outer surface, a steering member defining an inner surface, and a trolley member adapted to be connected to a steering wire and at least partially located between the handle body outer surface and the steering member inner surface. The trolley member is operably connected to the steering member such that the trolley member will be axially repositioned in response to rotation of the steering member about the handle body.

Such handle apparatus preferably include a fitting for a luer or other connector used to connect a tubular device to the handle apparatus and allow a catheter to pass therethrough. The trolley members in each apparatus move relative to the handle body and steering member to push or pull the steering wire distally or proximally. The handle body and steering member will not move longitudinally relative to one another when the steering member is rotated. As a result, handle body and sheath will not move longitudinally during steering operations as is the case with many conventional handles.

In order to accomplish some of these and other objectives, a handle apparatus in accordance with one embodiment of a present invention includes a handle body with at least one wing member. The wing member advantageously prevents the handle body from rotating or rolling relative to the patient.

In order to accomplish some of these and other objectives, a handle apparatus in accordance with one embodiment of a present invention includes a handle body and a strain relief including a plurality of spaced portions. Such a strain relief element may be integrally formed with the handle body, thereby eliminating some of the manufacturing steps and costs associated with conventional strain relief elements.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions.

The present inventions may be used within body lumens, chambers or cavities for diagnostic or therapeutic purposes in those instance where access to interior bodily regions is obtained through, for example, the vascular system or alimentary canal and without complex invasive surgical procedures. For example, the inventions herein have application in the diagnosis and treatment of conditions within the heart. The inventions herein also have application in the diagnosis or treatment of ailments of the gastrointestinal tract, prostrate, brain, gall bladder, uterus, and other regions of the body.

Figure 1:
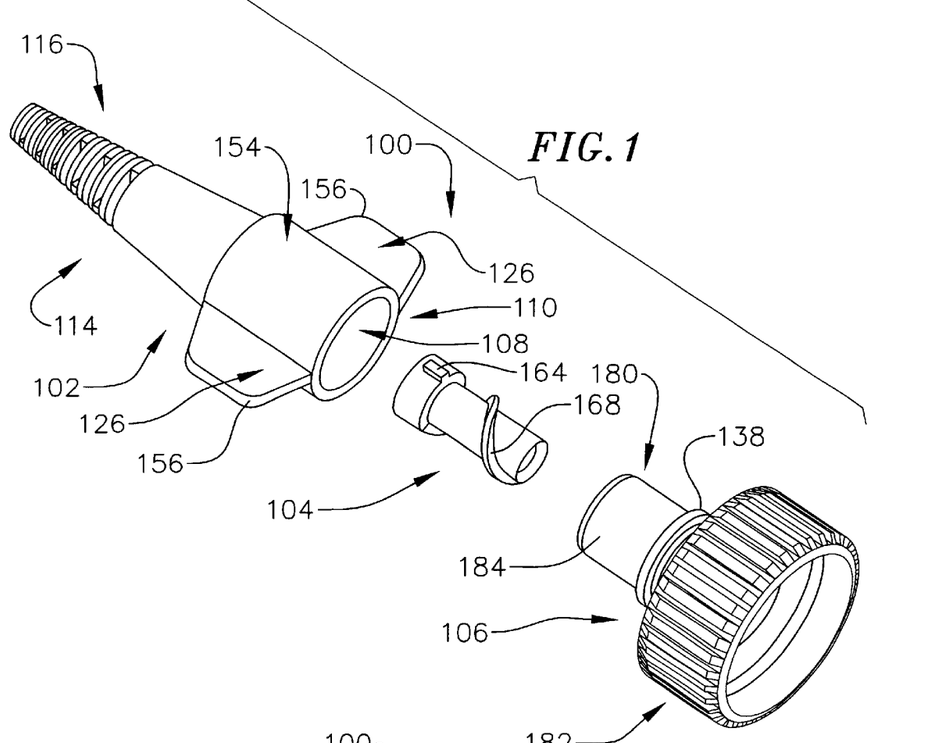
FIG. 1 is an exploded perspective view of a handle apparatus in accordance with a preferred embodiment of a present invention.
Figure 2:
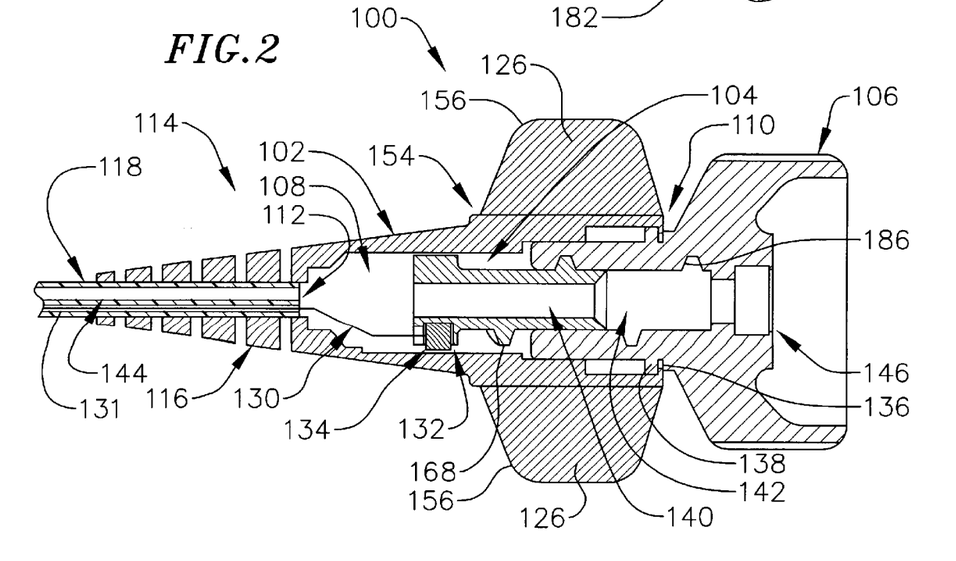
FIG. 2 is a section view of the handle apparatus illustrated in FIG. 1.
Figure 3:
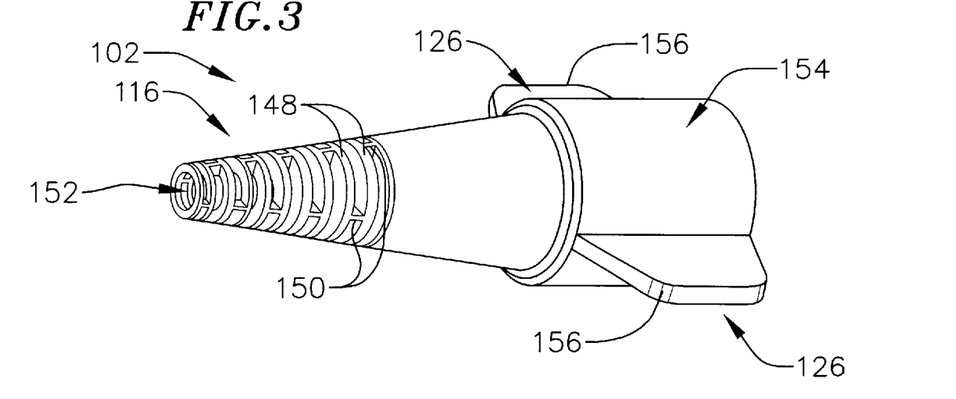
FIG. 3 is a perspective view of the handle body in the handle apparatus illustrated in FIG. 1.
Figure 4:
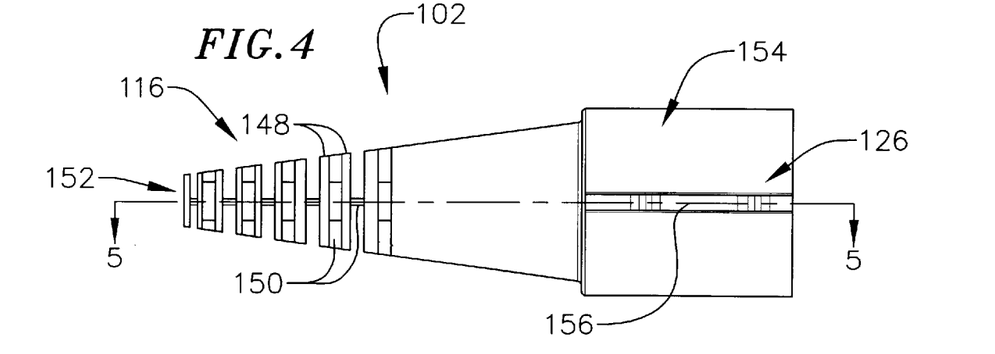
FIG. 4 is a side view of the handle body illustrated in FIG. 3.
Figure 5:
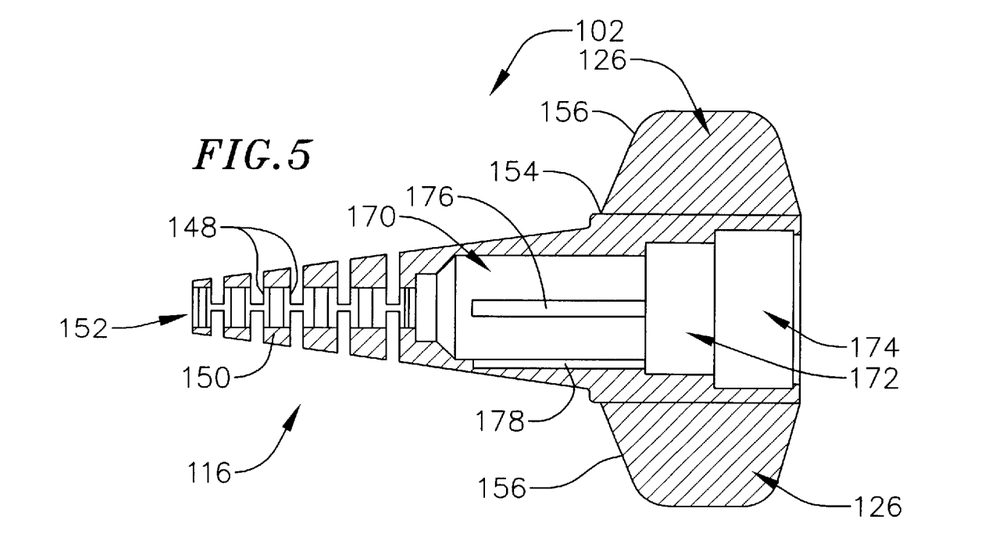
FIG. 5 is a section view taken along line 5—5 in FIG. 4.
Figure 6:
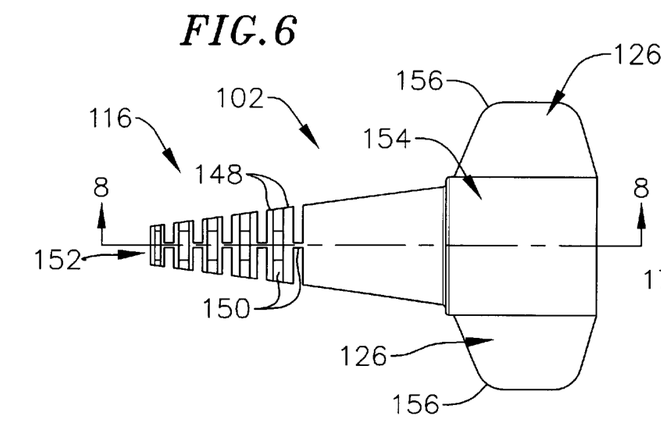
FIG. 6 is a top view of the handle body illustrated in FIG. 3.
Figure 7:
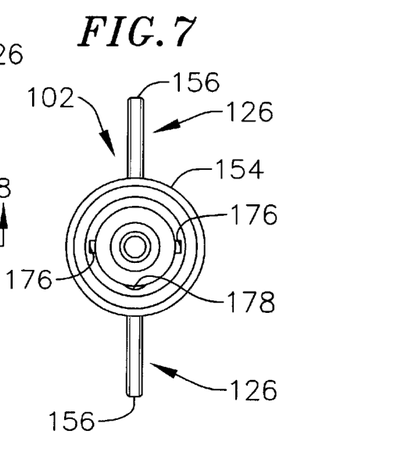
FIG. 7 is a rear view of the handle body illustrated in FIG. 3.
Figure 8:
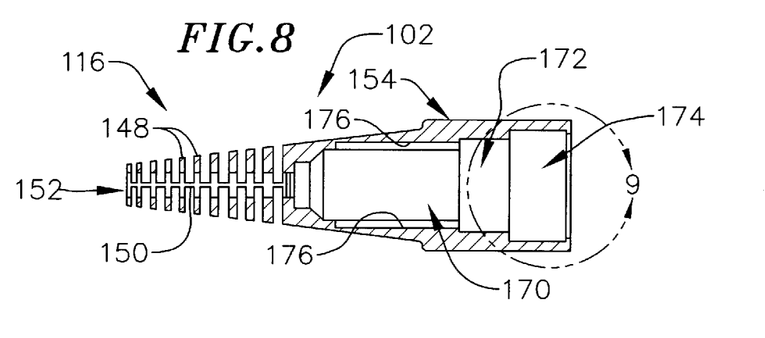
FIG. 8 is a section view taken along line 8—8 in FIG. 6.
Figure 9:
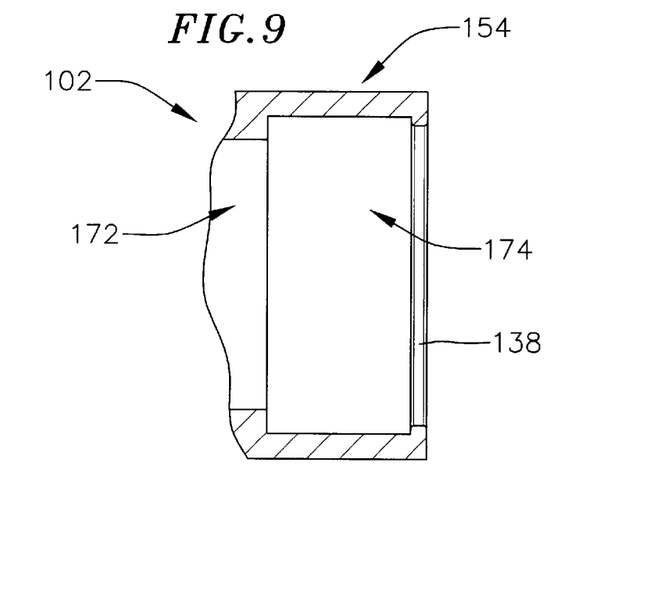
FIG. 9 is an enlarged view of the proximal portion of the handle body illustrated in FIG. 8.
Figure 10:
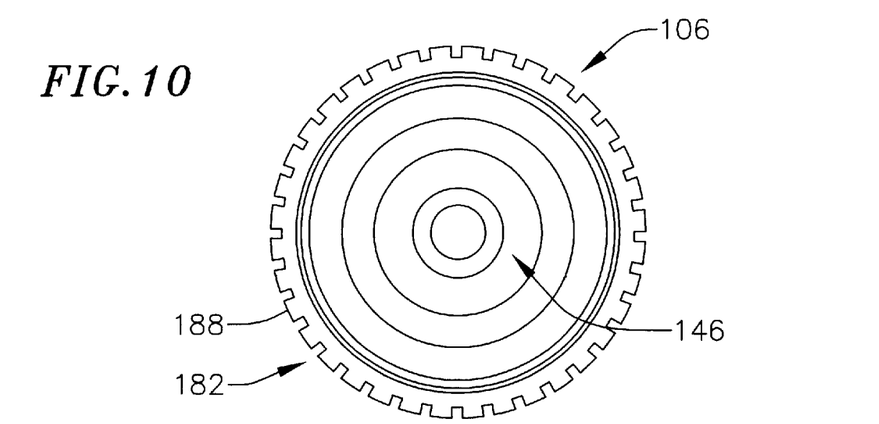
FIGS. 10–12 are rear, top and front views, respectively, of the steering member in the handle apparatus illustrated in FIG. 1.
Figure 11:
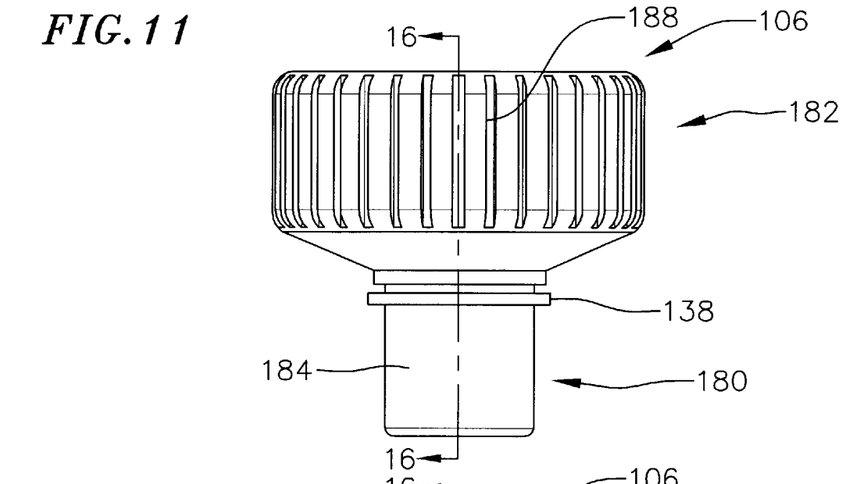
Figure 12:
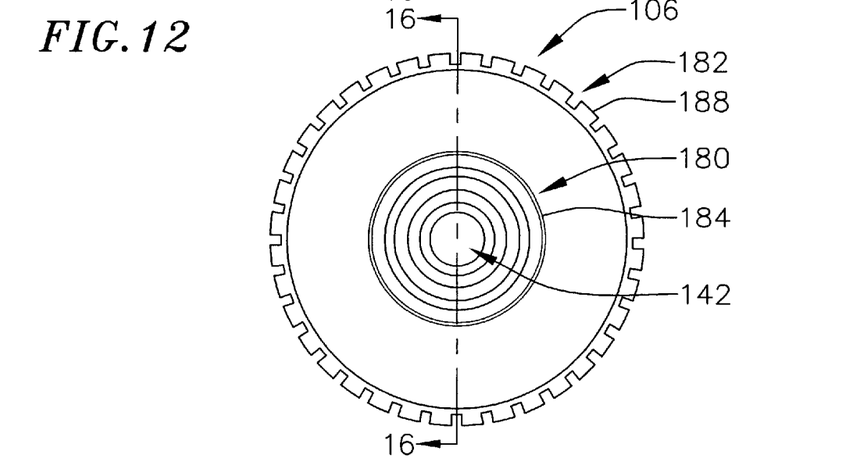
Figure 13:
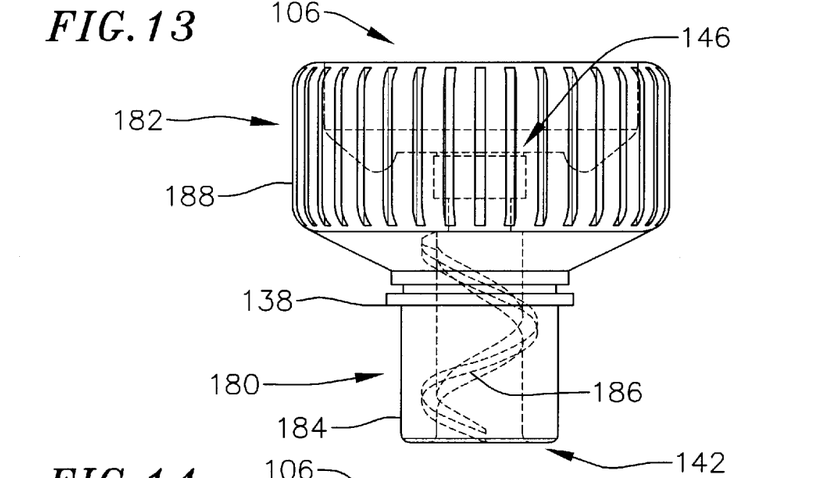
FIG. 13 is another top view of the steering member illustrated in FIGS. 10–12.
Figure 14:
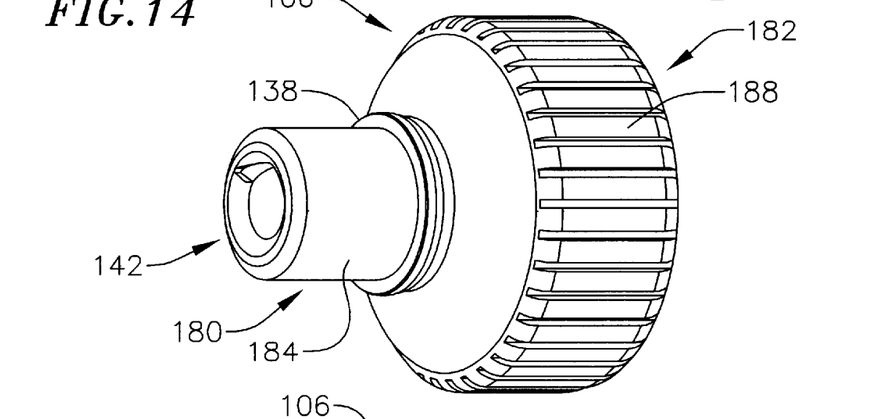
FIGS. 14 and 15 are perspective views of the steering member illustrated in FIGS. 10–12.
Figure 15:
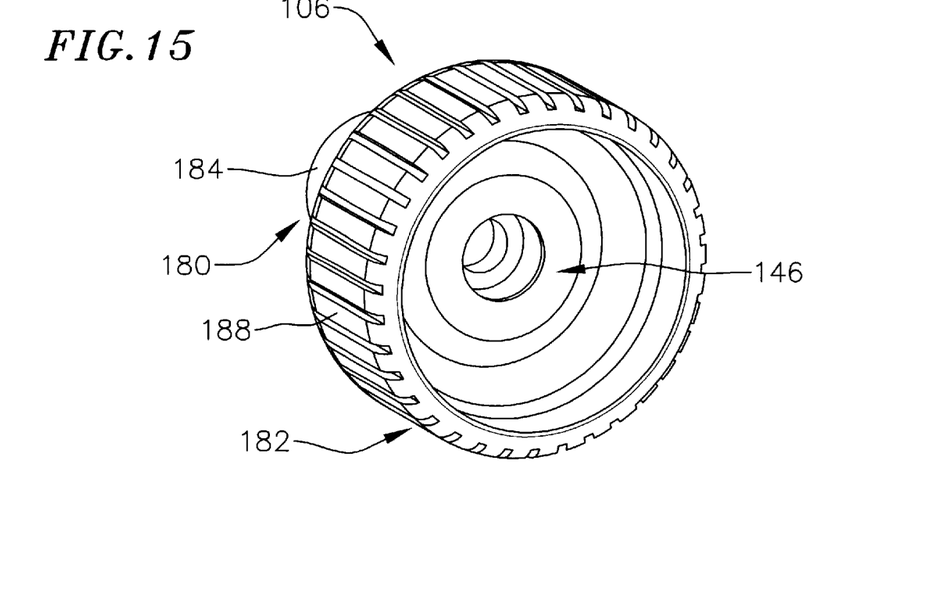
Figure 16:
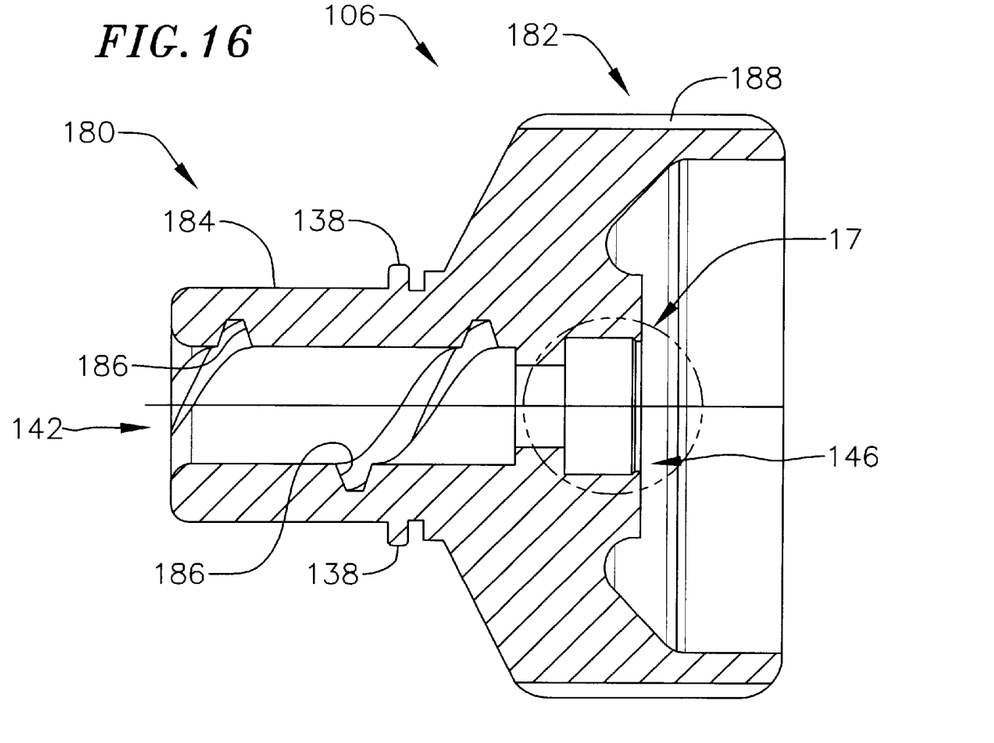
FIG. 16 is a section view taken along lines 16—16 in FIGS. 11 and 12.
Figure 17:
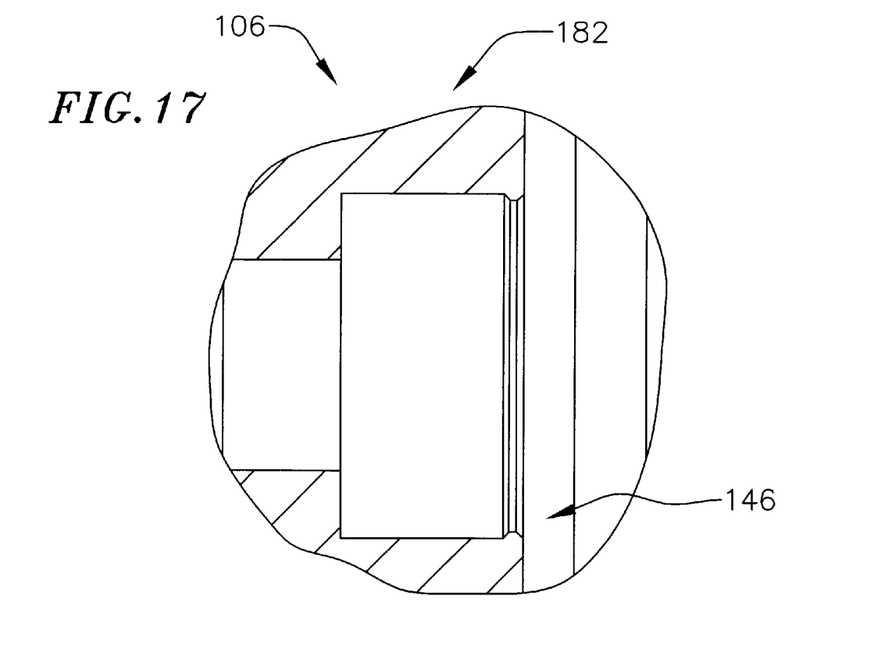
FIG. 17 is an enlarged section view of a proximal portion of the steering member illustrated in FIG. 16.
Figure 18:
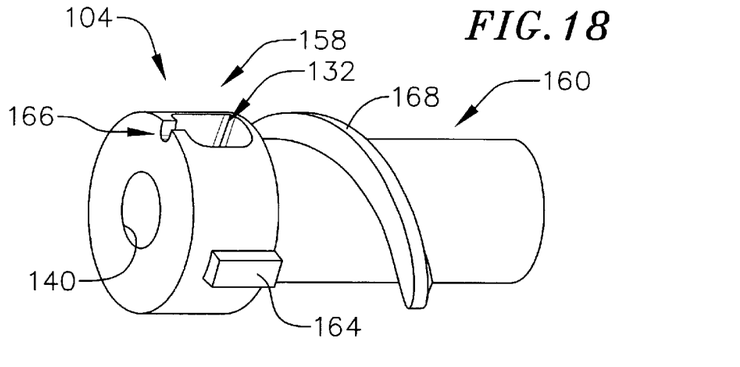
FIG. 18 is a perspective view of the trolley member in the handle apparatus illustrated in FIG. 1.
Figures 19, 20:
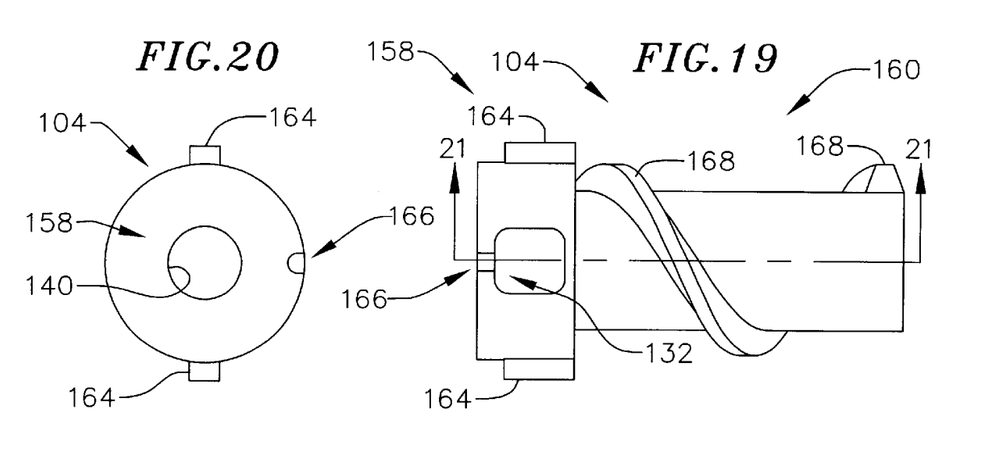
FIG. 19 is a side view of the trolley member illustrated in FIG. 18.
FIG. 20 is an end view of the trolley member illustrated in FIG. 18.
Figure 21:
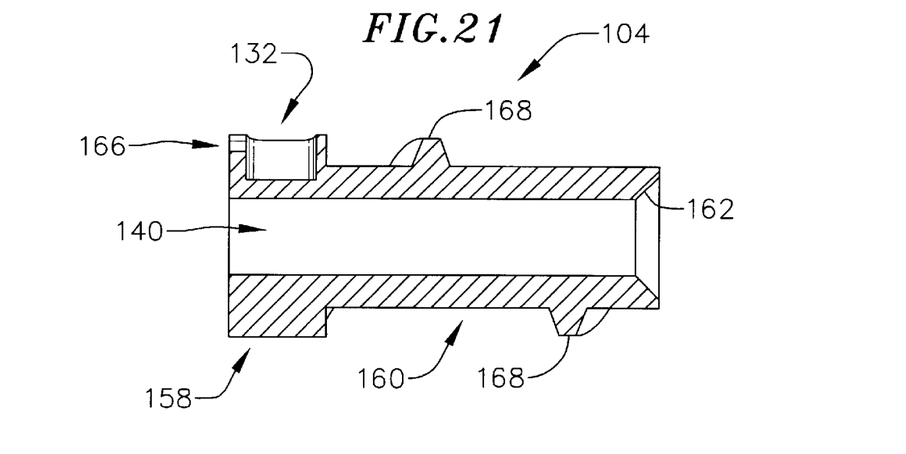
FIG. 21 is a section view taken along line 21—21 in FIG. 19.

As illustrated for example in FIGS. 1 and 2, a handle apparatus 100 in accordance with a preferred embodiment of a present invention includes a handle body 102, a trolley member 104 and a steering member 106.

The exemplary handle body 102 is formed with an inner chamber 108 that spans from the proximal end 110 of the handle body to an aperture 112 formed in the distal portion 114. The exemplary handle body 102 includes an integrally formed strain relief member (or "element") 116 that secures the handle body to a steerable device 118. A pair of wing members 126 are provided opposite sides of the handle body proximal portion 154 to prevent the handle body from rotating or rolling relative to the patient. The wing members 126 preferably have curved edges 156 to minimize the chances of scratching a patient's skin and are also large enough to serve as surfaces against which tape can be adhered to secure the handle apparatus 100 to a patient. The number, size, shape and thickness of the wing members 126, as well as the position of the wing members on the handle body 102, may be varied to accommodate different applications and materials. Additional details concerning the handle body 102 are provided below with reference to FIGS. 3–9.

The exemplary trolley member 104 is slidably located within the handle body inner chamber 108 and is coupled to a steering wire 130 from the steerable device 118. The trolley member 104 includes a recess 132 at its distal end sized to receive a steering wire terminal 134, such as a block-shaped anchor member, that is attached to the proximal end of the steering wire 130. The steering wire 130 may also be mechanically coupled to the trolley member 104 in other ways. For example, a set screw could be used that would allow the tension on the steering wire 130 to be fine tuned. Here, the handle body 102 would include a small window (not shown) through which the set screw could be adjusted. Additional details concerning the trolley member 104 are provided below with reference to FIGS. 18–21.

Figure 24:
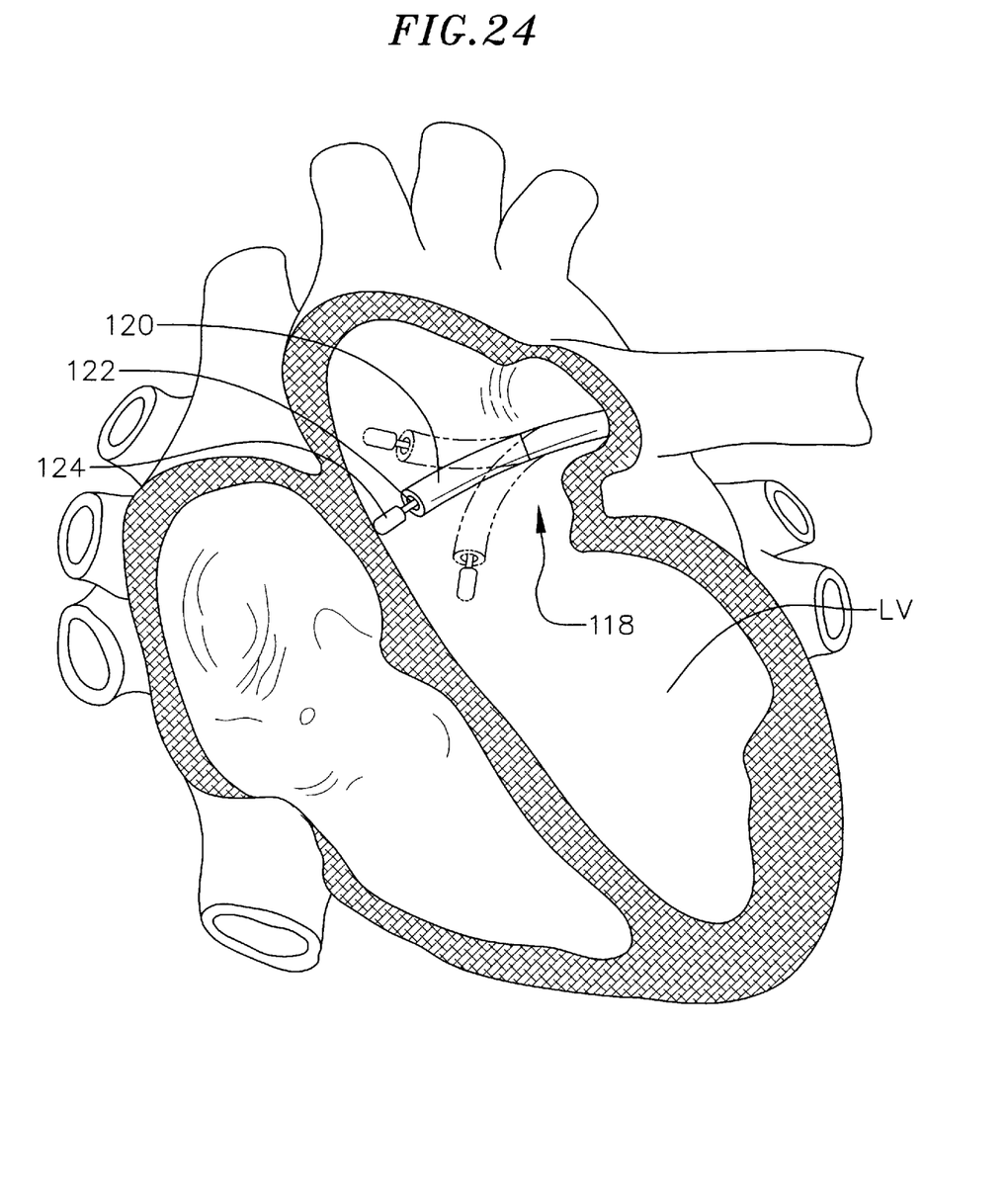
FIG. 24 is partial section view showing a steerable device and a catheter carrying a diagnostic or therapeutic element deployed within the heart.

The steering wire 130 extends through a steering wire lumen 131 to the distal portion 120 of the steerable device 118, which is illustrated in FIG. 24. The distal end of the steering wire 130 may be secured to the steerable device distal portion 120 by, for example, anchoring the steering wire to a metal ring within the distal end portion. Alternatively, an adhesive could be used to secure the steering wire 130 to the distal end of the steering wire lumen 131. A coil may also be provided within the distal portion 120 to help maintain the circular shape of the distal portion. Additional information concerning steerable devices and steering wires may be found in commonly assigned U.S. patent application Ser. No. 09/165,652, filed on Oct. 2, 1998, which is incorporated herein by reference.

The steering member 106, which is used to control movement of the steering wire 130, is rotatably coupled to the handle body 102 at its proximal end 110. In the exemplary embodiment, the proximal end 110 has a cantilevered edge portion 136 and the steering member 106 has a circumferential ridge 138. The cantilevered edge portion 136 and the circumferential ridge 138 are respectively shaped and sized such that the steering member 106 can be snap fitted into the handle body 102 and rotated relative thereto. A conventional o-ring seal (not shown) may be positioned adjacent the circumferential ridge 138. Additional details concerning the steering member 106 are provided below with reference to FIGS. 10–17.

The trolley member 104 serves as an intermediary mechanism between the steering wire 130 and steering member 106. More specifically, the exemplary trolley member 104 and steering member 106 are configured and positioned relative to each other such that rotation of the steering member relative to the handle body 102 will axially reposition the trolley member. Axial movement of the trolley member 104 will, in turn, either push or pull the steering wire 130 and deflect the steerable device distal portion 120. Referring to FIG. 24, the distal portion 120 may be inserted into the heart, steered into the vicinity of targeted tissue within the left ventricle LV, and repositioned as needed by rotating the steering member 106. A catheter 122 may then be inserted through a lumen 144 in the steerable device 118 and positioned such that an element 124 (such as a diagnostic and/or therapeutic electrode) is adjacent the targeted tissue.

In order to facilitate insertion of the catheter 122 into the steerable device lumen 144, the trolley member 104 and steering member 106 include respective lumens 140 and 142. The trolley member and steering member lumens 140 and 142 are axially aligned with the handle body aperture 112 and the steerable device lumen 144. So arranged, the steering member lumen 142, trolley lumen 140, inner chamber 108 and the handle body aperture 112 provide a continuous lumen through the handle apparatus 100. The steering member 106 is also shaped for mechanical coupling to a luer or other connector and, in the illustrated embodiment, includes a snap fit attachment portion 146. Other types of interfaces may be employed to accommodate other types of connectors.

Turning to FIGS. 3–8, the exemplary strain relief member 116, which is adapted to receive the proximal end of the steerable device 118, is more flexible than other parts of the handle body 102. The flexibility is achieved through the use of a plurality of disk-shaped portions 148 that are connected by ridges 150. Such a structure is, of course, more flexible than a solid structure formed from the same material with the same overall shape. There are preferably two interconnecting ridges 150 on each side of the disk-shaped portions 148 and the ridges are symmetrically staggered by 90 degrees from one pair of adjacent disk-shaped portions to the next. Each disk-shaped portion 148 also includes a centrally located aperture 152 adapted to receive the proximal portion of the steerable device 118. The strain relief member 116 narrows from its proximal end toward its distal end and is preferably, but not necessarily, integrally formed as part of the handle body 102 (e.g. a unitary molded part).

The disk-shaped portions 148 in the illustrated embodiment are about 0.02 inch thick and there is about 0.05 inch between adjacent disk-shaped portions. The ridges 150 are about 0.02 inch thick. These dimensions may be modified to accommodate different types of steerable devices 118 and material variations. The overall configuration of the strain relief member 116 may also be varied to suit particular needs. For example, the interconnecting ridges 150 can be staggered differently. The spaced portions 148 may also have other shapes other than disk-shaped. The number of disk-shaped portions 148, the manner in which the disk-shaped portions decrease in size moving toward the distal end of the strain relief member 116, and the number of ridges 150 between each pair of adjacent disk-shaped portions may also vary.

As illustrated in detail in FIGS. 18–21, the aforementioned trolley member recess 132 is preferably located in the trolley member distal portion 158. A conduit 166 extends from the trolley member recess 132 to the distal end of the trolley member. The conduit 166 is smaller than the steering wire terminal 134, which causes the steering wire terminal to be secured within the trolley member recess 132 in the manner illustrated in FIG. 2. The trolley member distal portion 158 and proximal portion 160 are both generally cylindrical in shape, with the distal portion having a larger outer diameter than the proximal portion. Although the trolley member distal portion 158 and portion of the inner chamber 108 adjacent thereto are generally cylindrical in shape, they can have other complementary shapes. A beveled edge 162 at the proximal end of the trolley member 104 facilitates insertion of diagnostic or therapeutic elements into the lumen 140.

The trolley member 104 also includes several structural elements that cooperate with portions of the handle body 102 and steering member 106. For example, at least one, and preferably two, generally rectangular tab members 164 are provided on opposite sides of the distal portion 158. The trolley member 104 also includes a spiral-shaped ridge (or "male thread") 168 formed about its proximal portion 160. The respective functions of the tab members 164 and spiral-shaped ridge 168 are discussed below.

With respect to the handle body 102, which is shown in detail in FIGS. 3–9, the inner chamber 108 includes a distal section 170, a central section 172 and proximal section 174. The inner dimensions of the inner chamber sections 170, 172, 174 correspond to the dimensions of the respective portions of the trolley member 104 and steering member 106 located therein. The distal inner chamber section 170 includes two tab channels 176 that are generally rectangular in shape and positioned on opposite sides of the distal inner chamber section. The tab members 164 on the trolley member 104 are adapted to fit within the tab channels 176. Alternatively, the trolley member 104 may include channels and the distal inner chamber section 170 may include tab members. In either case, the channels and tab members prevent the trolley member 104 from rotating relative to the handle body 102. A wire terminal channel 178 that accommodates the slight protrusion of the steering wire terminal 134 from the recess 132 (see FIG. 2) may also be provided in the distal inner chamber section 170.

Turning to FIGS. 10–17, the steering member 106 includes an engaging portion 180 with an outer surface 184 and a knob portion 182 with a gripping surface 188. The steering member 106 also includes a spiral-shaped groove (or "female thread") 186 with the lumen 142 that is complementary with the spiral-shaped ridge 168 on the trolley member 104. As rotation of the trolley member 104 is prevented by the tab members 164 and channels 176, the trolley member will slide axially in response to rotation of the steering member 106.

The handle body 102, the trolley member 104 and the steering member 106 are formed from materials, such as molded plastics, that are sufficiently lubricious to allow the proximal portion 160 of the trolley member 104 to slide within the engaging portion 180. With regard to the relative dimensions of the various elements of the exemplary handle apparatus 100, the outer diameter of the trolley member distal portion 158 (apart from the tab members 164) is slightly smaller than the inner diameter of the distal inner chamber section 170, the outer diameter of the steering member engaging portion 180 is slightly smaller than the inner diameter of the central inner chamber section 172, and the outer diameter of the circumferential ridge 138 is slightly smaller than the inner diameter of the proximal inner chamber section 174. Nevertheless, the materials and relative dimensions should be selected such that there will be sufficient friction between the threads 168 and 186 to maintain the distal portion of the steerable device 118 in a curved orientation when the steering is released by the physician.

The handle apparatus 100 illustrated in FIGS. 1–21 may be assembled as follows. First, the steerable device 118 is inserted into the handle body aperture 152, through the strain relief member 116, and though the open proximal end 110 with the steering wire 130 extending outwardly therefrom. The steering wire 130 is cut to the proper length and the steering wire terminal 134 is soldered onto the proximal end of the steering wire. Next, the steering wire terminal 134 is placed into the trolley member recess 132 and the tab members 164 on the trolley member 104 are then aligned with the tab channels 176. The steerable device 118 is then pulled proximally back through the handle body 102, with the trolley member 104, until the steerable device is positioned in the location illustrated in FIG. 2, where it is bonded in place. Finally, the steering member 106 is snapped into the handle body 102 and threaded onto the trolley member 104. Note that the handle body 102 may include a door or the like adjacent the steering wire terminal 134, for assembly and/or adjustment purposes.

Figure 22:
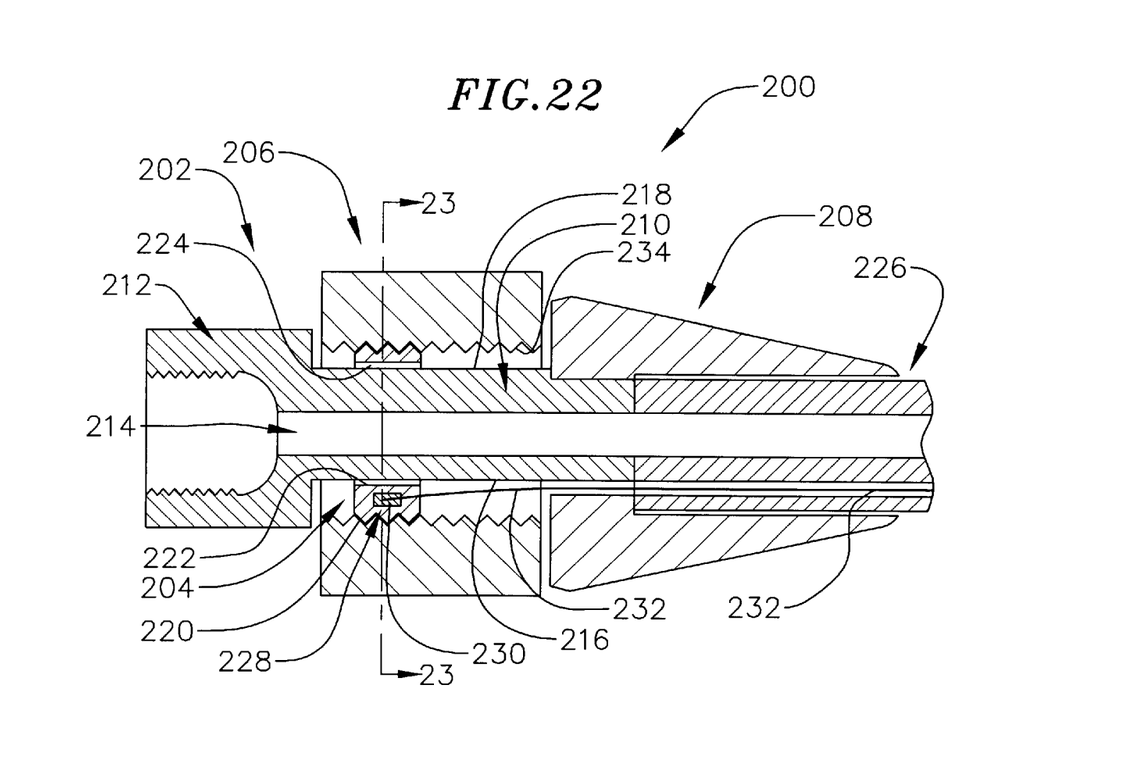
FIG. 22 is a side section view of a handle apparatus in accordance with a preferred embodiment of a present invention.
Figure 23:
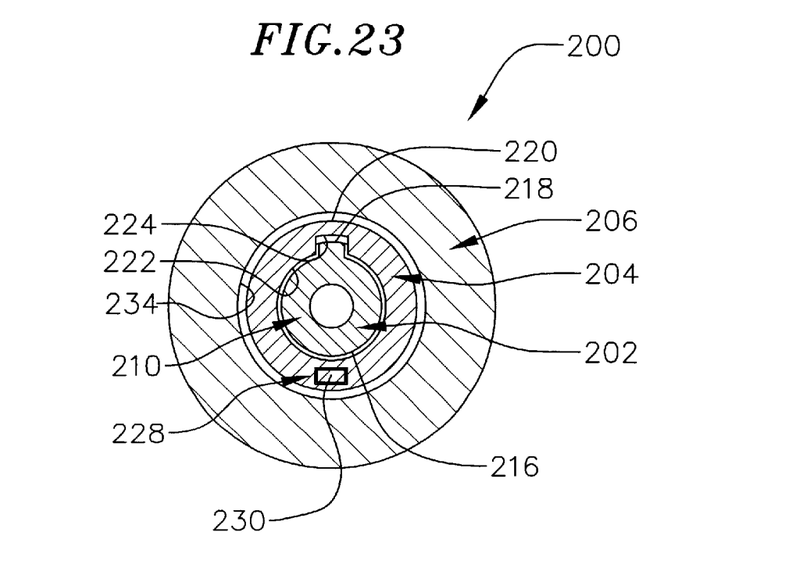
FIG. 23 is a section view taken along line 23—23 in FIG. 22.

Another exemplary handle apparatus, which is generally represented by reference numeral 200, is illustrated in FIGS. 22 and 23. Handle apparatus 200 includes a handle body 202, a trolley member 204, a steering member 206 and a strain relief element 208. Each of these elements, and the manner in which they cooperate with one another, are discussed in detail below. Although there are many structural differences between the two, handle apparatus 200 is functionally similar to the handle apparatus 100 illustrated in FIGS. 1–21 in that rotation of steering member 206 will result in axial movement of the trolley member 204 and, ultimately, deflection of the tip of the associated steerable device. The handle body 202, trolley member 204, and steering member 206 are preferably formed from molded plastic.

The exemplary handle body 202 includes a distal portion 210, a fitting portion 212 that facilitates mechanical coupling to a luer or other connector, and a lumen 214. The distal portion 210 includes an outer surface 216 that extends from the fitting portion 212 to the strain relief element 208 and an axial ridge 218 on the outer surface. The exemplary trolley member 204 includes a threaded outer surface 220 and an cylindrical inner surface 222 with an axial channel 224. The axial channel 224 rides on the axial ridge 218, thereby preventing rotation of the trolley member 204. Alternatively, the trolley member 204 may be provided with an axial ridge and the handle body outer surface 206 may be provided with an axial channel. The trolley member 204 also includes a recess 228 adapted to receive a steering wire anchor member 230 on the end of a steering wire 232 that extends from the steerable device 226. The exemplary steering member 206 is in the form of a knob which includes a threaded inner surface 234 that mates with the threaded trolley member outer surface 220. As such, and because rotation of the trolley member 204 is prevented by the ridge 218 and channel 224, rotation of the steering member 206 about the handle body 202 will axially reposition the trolley member and steering wire 232.

In the exemplary embodiment illustrated in FIGS. 22 and 23, the strain relief member 208 is secured to the steerable device 226 and to the handle body 202. The strain relief member 208, which should be more flexible than the handle body 202, is preferably a tapered solid piece of rubber or relatively soft plastic. Alternatively, the strain relief member 116 illustrated in FIGS. 1–9 may be employed.

The exemplary handle apparatus 200 illustrated in FIGS. 22 and 23 may be assembled as follows. The steerable device 226 is bonded to the strain relief element 208 with the steering wire 232 and the steering wire anchor member 230 extending therefrom. The distal portion of the steerable device 226 is then bent to force additional steering wire 232 from the steerable device. Next, the steering wire anchor member 230 is secured within the trolley member recess 228 and the steering member 206 is threaded over the trolley member 204. The handle body 202 may then be fitted through the trolley member 204 and the distal portion 210 of the handle body 202 bonded to the strain relief element 208.

Although the present inventions have been described in terms of the preferred embodiment above, numerous modifications and/or additions to the above-described preferred embodiments would be readily apparent to one skilled in the art. By way of example, but not limitation, the steering member in some implementations may be mounted on a shaft perpendicular to the axis of the main lumen and the steering wire wrapped around the shaft. It is intended that the scope of the present inventions extends to all such modifications and/or additions.

We claim:

1. A handle apparatus for use with a steerable device including a steerable device body and steering wire, the handle apparatus comprising:

a handle body adapted to be secured to the steerable device body and defining a proximal end, an inner chamber, a proximal aperture and a distal aperture;

a trolley member slidably located at least partially within the inner chamber and adapted to be connected to the steering wire, the trolley member defining a trolley member lumen substantially aligned with the handle body proximal and distal apertures; and a steering member rotatably coupled to handle body and operably connected to the trolley member such that rotation of the steering member axially repositions the trolley member, the steering member including a steering member lumen substantially axially aligned with the trolley member lumen and a knob defining a distal end that is proximal to the proximal end of the handle body.

2. A handle apparatus as claimed in claim 1, wherein the handle body includes a strain relief member.

3. A handle apparatus as claimed in claim 1, wherein the handle body includes at least one wing member.

4. A handle apparatus as claimed in claim 1, wherein the inner chamber includes a channel and the trolley member includes a tab member adapted to fit within the channel.

5. A handle apparatus as claimed in claim 1, wherein the steerable device defines a steerable device lumen and the handle body is adapted to secure the steerable device such that the steerable device lumen is substantially axially aligned with the trolley member lumen.

6. A handle apparatus as claimed in claim 1, wherein the steering member lumen includes a spiral-shaped groove and the trolley member includes a complimentary spiral-shaped ridge.

7. A handle apparatus as claimed in claim 1, wherein the steering member is adapted to be coupled to a connector.

8. A handle apparatus as claimed in claim 1, wherein the distal end of the knob is proximally spaced from the proximal end of the handle body.

9. A handle apparatus for use with a steerable device including a steerable device body and steering wire, the handle apparatus comprising:
   a handle body adapted to be secured to the steerable device body and defining an outer surface;
   a steering member defining an inner surface; and
   a trolley member adapted to be connected to the steering wire and at least partially located between the handle body outer surface and the steering member inner surface, the trolley member being operably connected to the steering member such that the trolley member will be axially repositioned in response to rotation of the steering member about the handle body.

10. A handle apparatus as claimed in claim 9, wherein the handle body includes a lumen extending axially therethrough.

11. A handle apparatus as claimed in claim 9, wherein the handle body is adapted to be coupled to a connector.

12. A handle apparatus as claimed in claim 9, wherein the steering member comprises a knob.

13. A handle apparatus as claimed in claim 9, wherein the steering member and the trolley member respectively include complementary threads.

14. A handle apparatus as claimed in claim 9, wherein the trolley member includes an axial channel and the outer surface of the handle body includes an axial ridge adapted to slide within the axial channel.

15. A handle apparatus as claimed in claim 9, wherein the steering wire includes an anchor and the trolley member includes a recess adapted to receive the anchor.

16. A handle apparatus as claimed in claim 9, further comprising:
   a strain relief element secured to a distal portion of the handle body.

17. A handle apparatus as claimed in claim 16, wherein the handle body includes a fitting adapted to be coupled to a connector and the handle body outer surface is located between the fitting and the strain relief element.

18. A handle apparatus for use with a steerable device including a steerable device body and steering wire, the handle apparatus comprising:
   a handle body defining a longitudinal axis and including a portion adapted to be secured to the steerable device and an outer surface with a region of maximum width in a direction transverse to the longitudinal axis;
   at least one wing member that extends outwardly from the outer surface of the handle body beyond the region of maximum width in a direction transverse to the longitudinal axis; and
   a steering member on the handle body and operably connected to the steering wire.

19. A handle apparatus as claimed in claim 18, wherein the at least one wing member comprises two wing members.

20. A handle apparatus as claimed in claim 19, wherein the wing members are positioned on opposite sides of the handle body.

21. A handle apparatus as claimed in claim 19, wherein the at least one wing member defines curved edges.

22. A handle apparatus as claimed in claim 18, wherein the handle body outer surface includes a region of minimum width in a direction transverse to the longitudinal axis.

23. A handle apparatus as claimed in claim 22, wherein the region of maximum width of the handle body outer surface is associated with the proximal portion of the handle body.

24. A handle apparatus for use with a steerable device including a steerable device body and steering wire, the handle apparatus comprising:
   a handle body including at least one wing member located on a proximal portion of the handle body and a portion adapted to be secured to the steerable device; and
   a steering member on the handle body and operably connected to the steering wire.

25. A handle apparatus for use with a steerable device including a steerable device body and steering wire, the handle apparatus comprising:
   a handle body including an integrally formed strain relief element adapted to be secured to the steerable device; and
   a steering member on the handle body operably connected to the steering wire.

26. A handle apparatus as claimed in claim 25, wherein the handle body comprises a unitary molded part.

27. A handle apparatus for use with a steerable device including a steerable device body and steering wire, the handle apparatus comprising:
   a handle body;
   a strain relief element associated with the handle body and adapted to be secured to the steerable device, the strain relief element including a plurality of spaced portions; and
   a steering member on the handle body operably connected to the steering wire.

28. A handle apparatus as claimed in claim 27, wherein the strain relief element defines proximal and distal ends and narrows from the proximal end toward the distal end.

29. A handle apparatus as claimed in claim 27, wherein the spaced portions comprise spaced disk-shaped portions.

30. A handle apparatus as claimed in claim 29, wherein the strain relief element includes ridges that interconnect the spaced disk-shaped portions.

31. A handle apparatus for use with a steerable device including a steerable device body and steering wire, the handle apparatus comprising:
   a handle body adapted to be secured to the steerable device body and defining an inner chamber, a proximal aperture and a distal aperture;
   a trolley member slidably located at least partially within the inner chamber and adapted to be connected to the steering wire, the trolley member defining a trolley member lumen substantially aligned with the handle body proximal and distal apertures;
   a steering member rotatably coupled to handle body and operably connected to the trolley member such that rotation of the steering member axially repositions the trolley member, the steering member including a steering member lumen substantially axially aligned with the trolley member lumen and a portion configured to be coupled to a connector.

32. A handle apparatus as claimed in claim 31, wherein the handle body includes a strain relief member.

33. A handle apparatus as claimed in claim 31, wherein the handle body includes at least one wing member.

34. A handle apparatus as claimed in claim 31, wherein the inner chamber includes a channel and the trolley member includes a tab member adapted to fit within the channel.

35. A handle apparatus as claimed in claim 31, wherein the handle body defines a proximal end, the steering member includes a knob portion extending from the proximal end of the handle body, and the portion configured to be coupled to a connector is associated with the knob portion.

36. A handle apparatus as claimed in claim 31, wherein the portion configured to be coupled to a connector is configured to be mechanically coupled to a connector.

37. A handle apparatus as claimed in claim 31, wherein the portion configured to be coupled to a connector is configured to be coupled to a luer connector.

38. A handle apparatus as claimed in claim 31, wherein the portion configured to be coupled to a connector defines an opening that is aligned with the steering member lumen.

* * * * *